(12) United States Patent
Holmström et al.

(10) Patent No.: US 8,133,187 B2
(45) Date of Patent: Mar. 13, 2012

(54) IMPLANTABLE MEDICAL DEVICE WITH HEART CONDITION DETECTION

(75) Inventors: Nils Holmström, Järfäila (SE); Kjell Noren, Solna (SE)

(73) Assignee: St. Jude Medical AB, Jarfalla (SE)

( * ) Notice: Subject to any disclaimer, the term of this patent is extended or adjusted under 35 U.S.C. 154(b) by 909 days.

(21) Appl. No.: 12/095,216

(22) PCT Filed: Dec. 16, 2005

(86) PCT No.: PCT/SE2005/001955
§ 371 (c)(1), (2), (4) Date: May 28, 2008

(87) PCT Pub. No.: WO2007/069961
PCT Pub. Date: Jun. 21, 2007

(65) Prior Publication Data
US 2008/0306566 A1    Dec. 11, 2008

(51) Int. Cl.
A61B 5/0255    (2006.01)
(52) U.S. Cl. ............. 600/528; 600/527; 607/18; 607/20
(58) Field of Classification Search .................. 600/527, 600/528; 607/18, 20
See application file for complete search history.

(56) References Cited

U.S. PATENT DOCUMENTS

| | | | |
|---|---|---|---|
| 6,048,319 A | 4/2000 | Hudgins et al. | |
| 6,409,675 B1 | 6/2002 | Turcott | |
| 6,527,729 B1 | 3/2003 | Turcott | |
| 6,643,548 B1 | 11/2003 | Mai et al. | |
| 2002/0151938 A1 | 10/2002 | Corbucci | |
| 2003/0055352 A1 | 3/2003 | Hayek et al. | |
| 2004/0127792 A1 | 7/2004 | Siejko et al. | |
| 2004/0138572 A1 | 7/2004 | Thiagarajan | |
| 2005/0148896 A1 | 7/2005 | Siejko et al. | |
| 2005/0222515 A1 | 10/2005 | Polyshchuk et al. | |
| 2006/0106322 A1 | 5/2006 | Arand et al. | |

FOREIGN PATENT DOCUMENTS

| | | |
|---|---|---|
| WO | WO 2004/032741 | 4/2004 |
| WO | WO 2004/035137 | 4/2004 |

OTHER PUBLICATIONS

"A Relative Value Method for Measuring and Evaluating Cardiac Reserve," Xiao et al., Biomed. Eng. Online, vol. 1, No. 6 (2002), Abstract.
"Functional Abnormalities is Isolated Left Bundle Branch Block. The Effect of Interventricular Asynchrony," Grines et al., Circulation, vol. 79, No. 4 (1989), Abstract.

*Primary Examiner* — Scott Getzow
*Assistant Examiner* — Joseph Dietrich
(74) *Attorney, Agent, or Firm* — Schiff Hardin LLP (57) ABSTRACT

A method for detecting a condition of a heart of a patient using an implantable medical device, including the steps of sensing acoustic signals indicative of heart sounds of the heart of the patient; extracting signals corresponding to a first heart sound (S1) and a second heart sound (S2) from sensed signals; calculating an energy value corresponding to a signal corresponding to the first heart sound (S1) and an energy value corresponding to the second heart sound (S2); calculating a relation between the energy value corresponding to the first heart sound and the energy value corresponding to the second heart sound for successive cardiac cycles; and using at least one relation to detect the condition or a change of the condition. A medical device for determining the posture of a patient and a computer readable medium encoded with instructions are used to perform the inventive method.

23 Claims, 8 Drawing Sheets

IMPLANTABLE MEDICAL DEVICE WITH HEART CONDITION DETECTION

BACKGROUND OF THE INVENTION

1. Field of the Invention

The present invention generally relates to implantable medical devices, such as cardiac pacemakers and implantable cardioverter/defibrillators, and in particular to a method, a medical device, a computer program product and a computer readable medium for detecting or deriving conditions or changes of conditions of a heart of a patient using detected heart sounds and corresponding energy values.

2. Description of the Prior Art

Auscultation is an important diagnostic method for obtaining information of the heart sounds, which is well established as diagnostic information of the cardiac function. The sounds are often described as S1-S4. During the working cycle of the heart mechanical vibrations are produced in the heart muscle and the major blood vessels. Acceleration and retardation of tissue cause the vibrations when kinetic energy is transformed to sound energy, e.g. at valve closing. Vibrations can also arise from turbulent blood flow, e.g. at stenosis and regurgitation. These vibrations may be listened to using a stethoscope or registered electronically using phonocardiography, i.e. graphical registration of the heart sounds by means of a heart microphone placed on the skin of the patient's thorax. Auscultation using a stethoscope is, to a large extent, built on practical experience and long practice since the technique is based on the doctor's interpretations of the hearing impressions of heart sounds. When applying phonocardiography, as mentioned above, a heart microphone is placed on the skin of the patient's thorax. In other words, it may be cumbersome and time-consuming to obtain knowledge of the heart sounds and the mechanical energy during the heart cycle using these manual or partly manual methods and, in addition, the obtained knowledge of the heart sounds may be inexact due to the fact that the knowledge is, at least to some extent, subjective.

The first tone S1 coincides with closure of the Mitral and Tricuspid valves at the beginning of systole. Under certain circumstances, the first tone S1 can be split into two components. An abnormally loud S1 may be found in conditions associated with increased cardiac output (e.g. fever, exercise, hyperthyroidism, and anemia), tachycardia and left ventricular hypertrophy. A loud S1 is also characteristically heard with mitral stenosis and when the P-R interval of the ECG is short. An abnormally soft S1 may be heard with mitral regurgitation, heart failure and first degree A-V block (prolonged P-R interval). A broad or split S1 is frequently heard along the left lower sternal border. It is a rather normal finding, but a prominent widely split S1 may be associated with right bundle branch block (RBBB). Beat-to-beat variation in the loudness of S1 may occur in atrial fibrillation and third degree A-V block.

The second heart sound S2 coincides with closure of the aortic and pulmonary valves at the end of systole. S2 is normally split into two components (aortic and pulmonary valves at the end of systole) during inspiration. Splitting of S2 in expiration is abnormal. An abnormally loud S2 is commonly associated with systemic and pulmonary hypertension. A soft S2 may be heard in the later stages of aortic or pulmonary stenosis. Reversed S2 splitting (S2 split in expiration—single sound in inspiration) may be heard in some cases of aortic stenosis but is also common in left bundle branch block (LBBB). Wide (persistent) S2 splitting (S2 split during both inspiration and expiration) is associated with right bundle branch block, pulmonary stenosis, pulmonary hypertension, or atrial septal defect.

The third heart sound S3 coincides with rapid ventricular filling in early diastole. The third heart sound S3 may be found normally in children and adolescents. It is considered abnormal over the age of 40 and is associated with conditions in which the ventricular contractile function is depressed (e.g. CHF and cardiomyopathy). It also occurs in those conditions associated with volume overloading and dilation of the ventricles during diastole (e.g. mitral/tricuspid regurgitation or ventricular septal defect). S3 may be heard in the absence of heart disease in conditions associated with increased cardiac output (e.g. fever, anemia, and hyperthyroidism).

The fourth heart sound S4 coincides with atrial contraction in late diastole. S4 is associated with conditions where the ventricles have lost their compliance and have become "stiff". S4 may be heard during acute myocardial infarction. It is commonly heard in conditions associated with hypertrophy of the ventricles (e.g. systemic or pulmonary hypertension, aortic or pulmonary stenosis, and some cases of cardiomyopathy). The fourth heart sound S4 may also be heard in patients suffering from CHF.

Thus, the systolic and diastolic heart functions are reflected in the heart sound. For example, in "A relative value method for measuring and evaluating cardiac reserve", Xiao S, Guo X, Sun X, Xiao Z, Biomed Eng Online, 2002 Dec. 6; 1:6. it was shown that the ratio of S1 amplitude after exercise to that at rest can be used to evaluate cardiac contractility and cardiac reserve mobilization level. It was also shown that the ratio of S1 amplitude to S2 amplitude (S1/S2) may be used as an indicator of hypotension. In "Functional abnormalities in isolated left bundle branch block. The effect of interventricular asynchrony", Grines C L, Bashore T M, Boudoulas H, Olson S, Shafer P, Wooley C F, Circulation, 1989 April; 79(4):845-53, it was shown that the first heart sound (S1) amplitude, expressed as the ratio S1/S2, was decreased in patients with isolated left bundle branch block (LBBB) due to wide separation of the valvular contributor to S1. Knowledge of the heart sounds and the mechanical energy as well as their relations during the heart cycle can thus be used for monitoring or detecting conditions or changes of conditions of a heart of a patient.

However, there is no known technique for continuously and automatically collecting information of the heart sounds, the corresponding energy values, and their relations and using the information to detect or derive detecting conditions or changes of conditions of a heart of a patient, such as, for example, heart insufficiency, systemic hypertension, or pulmonary hypertension.

SUMMARY OF THE INVENTION

Thus, an object of the present invention is to provide a method and medical device that are capable of continuously and automatically collecting information of the heart sounds and the corresponding energy values and their relations and to detect or derive conditions or changes of conditions of a heart of a patient using detected heart sounds and corresponding energy values.

According to an aspect of the present invention, there is provided an implantable medical device for detecting a condition of a heart of a patient, which device includes a pulse generator adapted to produce cardiac stimulating pacing pulses and the device being connectable to at least one lead carrying electrodes for delivering the pulses to cardiac tissue in at least one chamber of a heart of a patient. The device has a signal processing circuit adapted to extract signals corresponding to a first heart sound (S1) and a second heart sound (S2) from at least one sensed signal, the at least one sensed signal being received from an acoustic sensor adapted to sense an acoustic energy and to produce signals indicative of heart sounds of the heart of the patient over predetermined periods of a cardiac cycle during successive cardiac cycles, and to calculate an energy value corresponding to the first heart sound (S1) and an energy value corresponding to the second heart sound (S2); a storage unit that stores the energy values corresponding to the first heart sound and the second head sound; and a controller adapted to calculate a relation between the energy value corresponding to the first heart sound and the energy value corresponding to the second heart sound for successive cardiac cycles and to use at least one relation to detect the condition or a change of the condition.

According to a second aspect of the present invention, there is provided a method for detecting a condition of a head of a patient using an implantable medical device including a pulse generator adapted to produce cardiac stimulating pacing pulses and electrodes for delivering the pulses to cardiac tissue of the heart of the patient. The method includes the steps of sensing an acoustic energy using an acoustic sensor; producing signals indicative of heart sounds of the heart of the patient over predetermined periods of a cardiac cycle during successive cardiac cycles; extracting signals corresponding to a first heart sound (S1) and a second heart sound (S2) from a sensed signal of a cardiac cycle; calculating an energy value corresponding to a signal corresponding to the first heart sound (S1) and an energy value corresponding to the second heart sound (S2); storing the energy values corresponding to the first heart sound and the second heart sound; calculating a relation between the energy value corresponding to the first heart sound and the energy value corresponding to the second heart sound for successive cardiac cycles; and using at least one relation to detect the condition or a change of the condition.

According to a further aspect of the present invention, there is provided a computer readable medium encoded with programming instructions that cause a computer to perform a method according to the second aspect of the present invention.

Thus, the basis of the invention is, in an implantable medical device, collecting or obtaining information of energy values of the heart sounds and their relation, which carry valuable information of the workload and status of the heart, and using this information to detect different conditions and changes of such conditions. In particular, the invention is based on the insight that the relation between the mitral valve energy and the aortic valve energy provides a useful indication of the occurrence of different conditions and/or changes of such conditions. To this end, the relation R between the mitral valve energy E1, or in other words the energy corresponding to the first heart sound S1, and the aortic valve energy E2, i.e. the energy corresponding to the second heart sound S2, has been found to constitute a useful indicator.

This invention provides several advantages. For example, one advantage is that the collecting of information and the determining or detecting of conditions or changes of conditions can be performed on a continuous and automated basis.

Another advantage is that changing conditions of a heart of a patient can be detected or derived at a relatively early stage and in a fast and reliable way since intrinsic information of the heart, i.e. the heart sounds, is used as input information, in turn, leading to a better security for the diagnosis for patients in different situations. The results is also accurate due to the facts that the systolic and diastolic heart functions are reflected in the heart sound, and that the heart sounds and their relations thus carry information of the workload and status of the heart.

The fact that the heart sounds are obtained by means of an implantable medical device connectable to an acoustic sensor that senses sounds or vibrations inside or outside the heart also contributes to higher degree of accuracy and reliability.

A further advantage of the present invention is that it is possible to study changes of the energy over time, which may provide useful information regarding, for example, the variability of the energy parameters. This information can, in turn, be used as an indicator of, for example, a changed filling due to e.g. arrhythmia or conduction disorder. Furthermore, the collected energy information can be used to tune a combination of drugs given to the patient.

According to an embodiment of the present invention, a present relation is compared with preceding relations to detect the condition or a change of the condition. Thus, the relation $R=E1/E2$ is a relative value that is compared with values in the pre-history. It is also possible to monitor the variability of the relation and the individual energy values. A high variability may indicate that filling is altering due to e.g. arrhythmia or conduction disorder.

In an embodiment of the present invention, a relation between a maximum amplitude of a first heart sound and a maximum amplitude of a second heart sound of a cardiac cycle is calculated for successive cardiac cycles and a present relation is compared with preceding relations in order to detect the condition or a change of the condition.

According to yet another embodiments of the present invention, each relation of energy values is calculated as a mean value over a predetermined number of successive relations of energy values corresponding to successive first heart sounds and second heart sounds. Each energy value can be calculated as a mean value over a predetermined number of successive energy values corresponding to successive first heart sound signals and second heart sounds signals. Thereby, more reliable and accurate energy values can be obtained. Alternatively, a weighted average value of a predetermined number of successive energy values can be used. In still another embodiment, a moving average of a predetermined number of successive energy values is utilized.

According to embodiments of the present invention, conditions including heart insufficiency, systemic hypertension, pulmonary hypertension, myocardial ischemia, increased cardiac output and/or increased stress level may be detected or derived. Changes in these conditions may also be detected or derived. In particular, if R becomes small it may thus be caused by a low E1 and/or a high E2. A low E1 may under this condition (i.e. a small R) be an indication of, for example, mitral regurgitation, a long PV interval (AV block III) or heart insufficiency and a high E2 may under this condition (i.e. a small R) be an indication of, for example, systemic pulmonary hypertension. The R-value will also decrease at myocardial ischemia, which may be used to detect silent ischemia. If R becomes high it may thus be caused by a high E1 and/or a low E2. A high E1 may under this condition (i.e. a high R) indicate, for example, increased cardiac output (CO), tachycardia, left ventricle hypertrophy, mitral stenosis, or a short PR interval. On the other hand, a small E2 (at a high R) may be an indication of aortic pulmonary stenosis.

In an alternative embodiment of the present invention, a present energy value corresponding to the first heart sound is compared with energy values corresponding to preceding first heart sounds and a present energy value corresponding to the second heart sound is compared with energy values corresponding to preceding second heart sounds in order to detect the condition or a change of the condition. Thus, information of individual energy values is used together with information of the relation between the values and thereby, the accuracy and reliability of the detection of a condition or a change of a conditions can be improved. For, example, in case of a low R value, a high E2 value may indicate systemic or pulmonary hypertension whereas a high E1 value may be an indication of stress or increased cardiac output at exercise In yet another embodiment of the present invention, at least one bandpass filter is adapted to filter off frequency components of the acoustic signal outside a predetermined frequency range. The at least one bandpass filter may have a frequency range of 10 to 300 Hz. If two bandpass filters are used, a first filter may be adapted to cut out a predetermined frequency range corresponding to typical frequencies for the first heart sound, for example, 20-40 Hz, and a second bandpass filter may be adapted to cut out a predetermined frequency range corresponding to typical frequencies for the second heart sound, for example, 20-100 Hz, or 10-300 Hz. The filtered signal (or signals) is rectified to produce at least one signal containing only positive or zero values and at least one local maximum point being coincident with a first heart sound signal and at least one local maximum point being coincident with a second heart sound signal are identified in the rectified signal (or signals). To produce the energy values corresponding to the specific first and second heart sounds, the sound signal (or signals) can be integrated in predetermined time windows comprising the at least one local maximum points, respectively, or in one predetermined time window comprising the local maximum points.

Alternatively, a squaring procedure is performed on the filtered signal (or signals) to produce at least one signal containing only positive or zero values. At least one local maximum point being coincident with a first heart sound signal and a second heart sound signal, respectively, are identified in the squared signal (or signals). To produce the energy values corresponding to the specific first and second heart sounds, the sound signal (or signals) can be integrated in predetermined time windows comprising the at least one local maximum points, respectively, or in one predetermined time window comprising the local maximum points.

In another embodiment of the present invention, at least one activity level of the patient is sensed and it is checked or determined whether the activity level is below a predetermined activity level. The activity level information is used in the detection or deriving of the condition or change of the condition. Alternatively, it is determined or checked whether the activity level is below a predetermined first activity level or within a activity level range between a second activity level and a third activity level and the activity level information is used in the detection or deriving of the condition or change of the condition. For example, a sensing session of the acoustic sensor can be synchronized with a determination that the sensed activity level is below the predetermined activity level an/or that the sensed activity level is within a activity level range between a second activity level and a third activity level. Thereby, it is possible to perform calculations of the relation R at stable conditions. This predetermined activity level can, for example, be set such that an activity level below the predetermined level indicates rest. The activity level information may be used to further enhance the accuracy of the condition determination. For example, since a high R value may be an indication of either increased cardiac output at exercise or an increased stress level of the patient, a high activity level indicating that the patient is exercising can be used together with a high R value to distinguish between these two conditions.

In an alternative embodiment of the present invention, at least one body position of the patient is detected and it is determined whether the patient is in at least one predetermined specific body position. In one embodiment of the present invention, the position detecting means is a back-position sensor arranged to sense when the patient is lying on his/hers back (or on his or hers face). The position information may be used in the detection or deriving of the condition or change of the condition. Moreover, a sensing session of the acoustic sensor may be synchronized with a determination that the patient is in a predetermined position. Thereby, it is possible to perform calculations of the relation R at stable conditions. Of course, one or more positions can be detected, for example, when the patient is in supine (lying down) and when the patient is in an upright position and thus one relation R can be obtained for the supine position and one relation R can be obtained for the upright position.

In yet another embodiment of the present invention, a heart rate of the patient is sensed and it is determined or checked whether a sensed heart rate is within a predetermined heart rate interval. The heart rate information can be used in the detection or deriving of a condition or change of a condition. A sensing session of the acoustic sensor can be synchronized with a determination that the sensed heart rate level is within a predetermined heart rate level range, below a predetermined heart rate level or above a predetermined heart rate level. Thereby, it is possible to perform calculations of the relation R at stable conditions.

In embodiments of the present invention, the acoustic sensor is arranged in a lead connectable to the device and is located e.g. in the right ventricle of the heart of the patient, or in a coronary vein of said patient, for example, on the epicardial surface in the coronary vein. Other locations is also possible, for example, the sensor may be placed in the right atrium or in the left ventricle According to embodiments of the present invention, the acoustic sensor is an accelerometer, a pressure sensor or a microphone.

In an alternative embodiment of the present invention, the sensor is arranged within the housing of the implantable device.

As will be apparent to those skilled in the art, the methods of the present invention, as well as preferred embodiments thereof, are suitable to realize as a computer program or a computer readable medium.

The features that characterize the invention, both as to organization and to method of operation, together with further objects and advantages thereof, will be better understood from the following description used in conjunction with the accompanying drawings. It is to be expressly understood that the drawings are for the purpose of illustration and description and is not intended as a definition of the limits of the invention. These and other objects attained, and advantages offered, by the present invention will become more fully apparent as the description that now follows is read in conjunction with the accompanying drawings.

DESCRIPTION OF THE PREFERRED EMBODIMENTS

Figure 1:
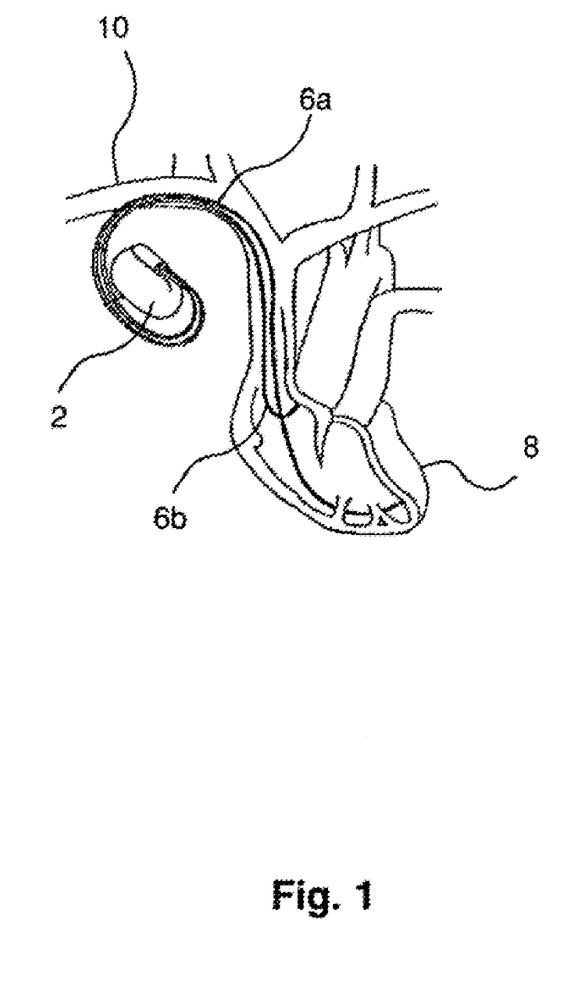
FIG. 1 is schematic diagram showing a medical device implanted in a patient in which device the present invention can be implemented.

With reference to FIG. 1, there is shown a schematic diagram of a medical device implanted in a patient in which device the present invention can be implemented. As can be seen, this embodiment of the present invention is shown in the context of a pacemaker 2 implanted in a patient (not shown). The pacemaker 2 has a housing being hermetically sealed and biologically inert. Normally, the housing is conductive and may, thus, serve as an electrode. The pacemaker 2 is connectable to one or more pacemaker leads, where only two are shown in FIG. 1 namely a right ventricular lead 6a and a right atrial lead 6b. The leads 6a and 6b can be electrically coupled to the pacemaker 2 in a conventional manner. The leads 6a, 6b extend into the heart 8 via a vein 10 of the patient. One or more conductive electrodes for receiving electrical cardiac signals and/or for delivering electrical pacing to the heart 8 are arranged near the distal ends of the leads 6a, 6b. As will be apparent to those skilled in the art, the leads 6a, 6b may be implanted with its distal end located in either the atrium or ventricle of the heart 8, or in the coronary sinus or in the great cardiac vein, or they may be in form of epicardial leads attached directly at the epicardium With reference now to FIG. 2, the configuration including the primary components of an embodiment of the present invention will be described. The illustrated embodiment comprises an implantable medical device 20, such as the pacemaker shown in FIG. 1. Leads 26a and 26b, of the same type as the leads 6a and 6b shown in FIG. 1, are connectable to the device 20. The leads 26a, 26b may be unipolar or bipolar, and may include any of the passive or active fixation means known in the art for fixation of the lead to the cardiac tissue. As an example, the lead distal tip (not shown) may include a tined tip or a fixation helix. The leads 26a, 26b comprises one or more electrodes (as described with reference to FIG. 1), such as a tip electrode or a ring electrode, arranged to, inter alia, measure the impedance or transmit pacing pulses for causing depolarization of cardiac tissue adjacent to the electrode(-s) generated by a pace pulse generator 25 under influence of a controller 27 including a microprocessor. The controller 27 controls, inter alia, pace pulse parameters such as output voltage and pulse duration.

Figure 2:
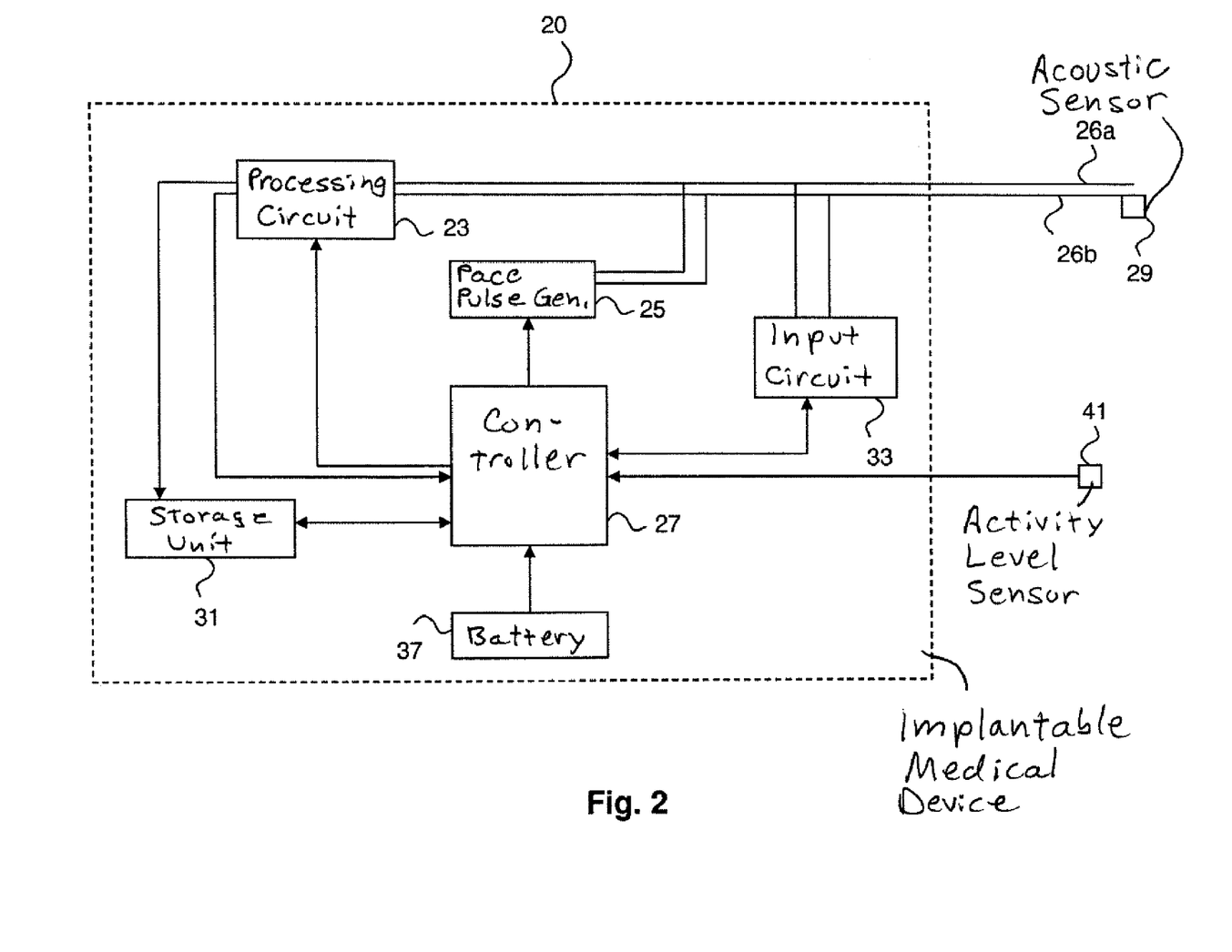
FIG. 2 is block diagram of the primary functional components of a first embodiment of the medical device according to the present invention.

Furthermore, an acoustic sensor 29 is arranged in or connected to one of the leads 26a, 26b, connectable to the device. Alternatively, the acoustic sensor can be located within the housing of the device 20. In one embodiment, the acoustic sensor 29 is arranged in a lead located at the left ventricle of the patient, for example, in the coronary vein on the left ventricle. Thereby, it is possible to accentuate the mitral sound and the aortic sound. According to examples, the acoustic sensor 29 is an accelerometer, a pressure sensor or a microphone. The acoustic sensor 29 is adapted to sense acoustic energy of the heart and to produce signals indicative of heart sounds of the heart of the patient. For example, the acoustic sensor 29 may sense the acoustic energy over predetermined periods of a cardiac cycle during successive cardiac cycles. In one embodiment of the present invention, a sensing session to obtain a signal indicative of a first heart sound (S1) and a second heart sound (S2) is synchronized with a detected heart event, e.g. detection of an intrinsic or paced QRS-complex. Thus, the signal is measured during a time window with a predetermined length being synchronized with the detection of the QRS-complex.

In another embodiment, a first sensing session to obtain a first signal indicative of a first heart sound (S1) is synchronized with a detection of an intrinsic or paced QRS-complex and a second sensing session to obtain a second signal indicative of a second heart sound (S2) is synchronized with a detection of an onset (or offset) of an T-wave within the same cardiac cycle. In other words, the signals are measured during two time windows with predetermined lengths, the first being synchronized with the detection of the QRS-complex and the second being synchronized with the detection of the T-wave. This will be discussed in further detail hereinafter with reference to FIGS. 6a and 6b.

Furthermore, the implantable medical device 20 comprises a signal processing circuit 23 adapted to process sensed signals received from the acoustic sensor 29. Embodiments of the signal processing circuit 23 are shown in FIGS. 3a, 3b and 3c.

Figure 3A:
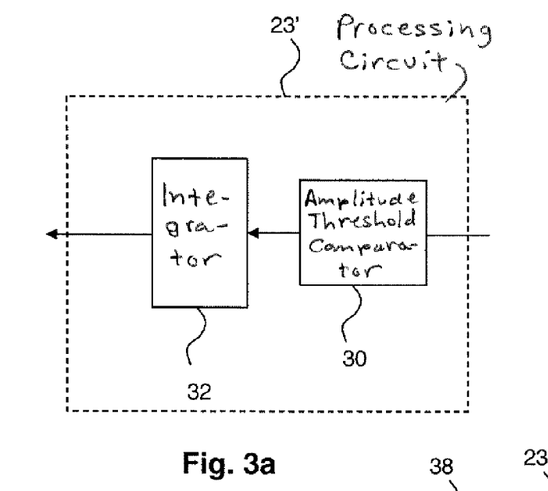
FIGS. 3a, 3b, and 3c are block diagrams of embodiments of a signal processing circuit according to the present invention.

According to one embodiment, see FIG. 3a, the signal processing circuit 23' has an amplitude threshold comparator circuit 30 adapted to determine signals corresponding to a first heart sound (S1) and a second heart sound (S2) of a sensed signal to be parts of the sensed signal having an amplitude above a predetermined amplitude level. The circuit 23' also has an integrator 32 adapted to integrate a sensed signal during a first predetermined time window to calculate an energy value corresponding to the first heart sound signal and during a second predetermined time window to calculate or produce an energy value corresponding the second heart sound signal.

Figure 3B:
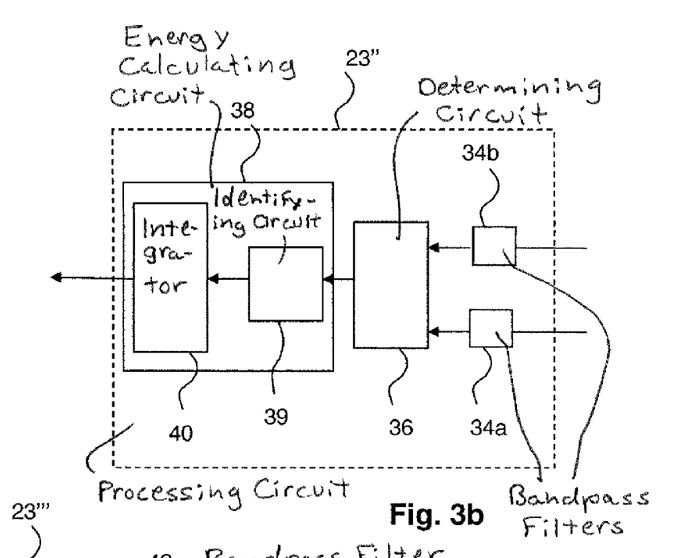

In another embodiment, see FIG. 3b, the signal processing circuit 23" includes pre-processing circuits including one or several bandpass filters 34a and 34b adapted to filter out frequency components of the sensed signals outside a predetermined frequency range and a determining circuit 36 adapted to determine the absolute value of the bandpass filtered signal and to produce a resulting absolute value heart sound signal. The bandpass filters may be a digital filter of second order and adapted to perform a zero-phase procedure to cancel out time delays introduced by the filters. In one embodiment, the signal processing circuit 23" includes two bandpass filters 34a and 34b. A first bandpass filter 34a is adapted to cut out a predetermined frequency range corresponding to typical frequencies for the first heart sound, for example, 20-40 Hz, and a second bandpass filter 34b is adapted to cut out a predetermined frequency range corresponding to typical frequencies for the second heart sound, for example, 20-100 Hz, or 10-300 Hz. The bandpass filtered signal or signals are fed to an absolute value determining means 36 adapted to determine an absolute value (or values) of the incoming signal (or signals) to produce a signal or signals having only positive or zero values. As alternatives to the determining unit, a rectifier can be used to rectify the filtered signal to obtain the instantaneous power of the filtered signal. Furthermore, the signal processing circuit 23" also includes an energy calculating circuit 38 adapted to calculate an energy value corresponding to the filtered signal. For example, the energy calculating circuit 38 may include an identifying circuit 39 adapted to identify at least one local maximum point being coincident with a first heart sound (S1) and at least one local maximum point being coincident with a second heart sound (S2) and an integrator 40 adapted to integrate the first heart sound signal in a predetermined time window encompassing the at least one local maximum point and the second heart sound signal in a predetermined time window comprising the at least one local maximum point, wherein an energy value of respective filtered signal can be obtained.

Figure 3C:
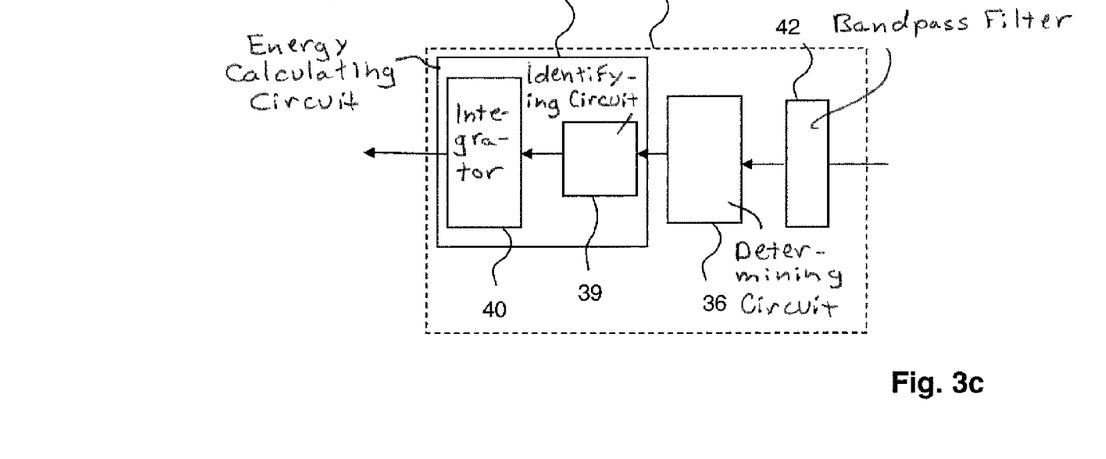

In yet another embodiment, see FIG. 3c, the signal processing circuit 23''' has pre-processing circuits including one bandpass filter 42 adapted to filter off frequency components of the sensed signals outside a predetermined frequency range and a determining circuit 36 adapted to determine the absolute value of the bandpass filtered signal and to produce a resulting absolute value heart sound signal. The bandpass filter 42 may be a digital filter of second order and adapted to perform a zero-phase procedure to cancel out time delays introduced by the filter. The bandpass filter 42 may be adapted to cut out a predetermined frequency range corresponding to typical frequencies for the first and second heart sound, for example, 10-300 Hz. The bandpass filtered signal is fed to a absolute value determining means 36 adapted to determine an absolute value (or values) of the incoming signal (or signals) to produce a signal or signals having only positive or zero values. As alternatives to the determining means, a rectifier can be used to rectify the filtered signal or the filtered signal can be squared. The signal processing circuit 23''' also comprises an energy calculating circuit 38 adapted to calculate an energy value corresponding to the filtered signal. For example, the energy calculating circuit 38 may include an identifying circuit 39 adapted to identify at least one local maximum point being coincident with a first heart sound (S1) and at least one local maximum point being coincident with a second heart sound (S2) and an integrator 40 adapted to integrate the signal over a predetermined time window comprising the local maximum points and the second heart sound signal in a predetermined time window comprising the at least one local maximum point, wherein an energy value of respective filtered signal can be obtained.

Returning now to FIG. 2, a storage means 31 is connected to the controller 27, which storage means 31 may include a random access memory (RAM) and/or a non-volatile memory such as a read-only memory (ROM). Storage means 31 is connected to the controller 27 and the signal processing circuit 23. Successive energy values corresponding to a signal corresponding to a first heart sound (S1) and an energy value corresponding to a second heart sound (S2) and/or extracted signals corresponding to a first heart sound (S1) and a second heart sound (S2) can thus be stored in the storing means 31.

Detected signals from the patient's heart are processed in an input circuit 33 and are forwarded to the controller 27 for use in logic timing determination in known manner. The implantable medical device 20 is powered by a battery 37, which supplies electrical power to all electrical active components of the medical device 20. Data contained in the storage means 31 can be transferred to a programmer (not shown) via a programmer interface (not shown) for use in analyzing system conditions, patient information, etc.

The medical device 20 according to the present invention may also include alarm means (not shown) adapted to send an alarm signal indicating that a specific condition has been detected or if a change of a specific condition has been detected. That is, the controller sends a triggering command to the alarm means if a specific condition has been detected or if a change of a specific condition has been detected. The alarm means may be a vibrator causing the device to vibrate or it may be adapted to deliver a beeping sound in order to alert the patient of the situation. Furthermore, an alarm signal can, for example, also or instead be sent to the programmer (not shown) via the programmer interface (not shown). The external unit, i.e. the programmer may be in contact with a central monitoring unit, e.g. at the hospital. In another embodiment, the alarm means is integrated into the controller 27.

Figure 4:
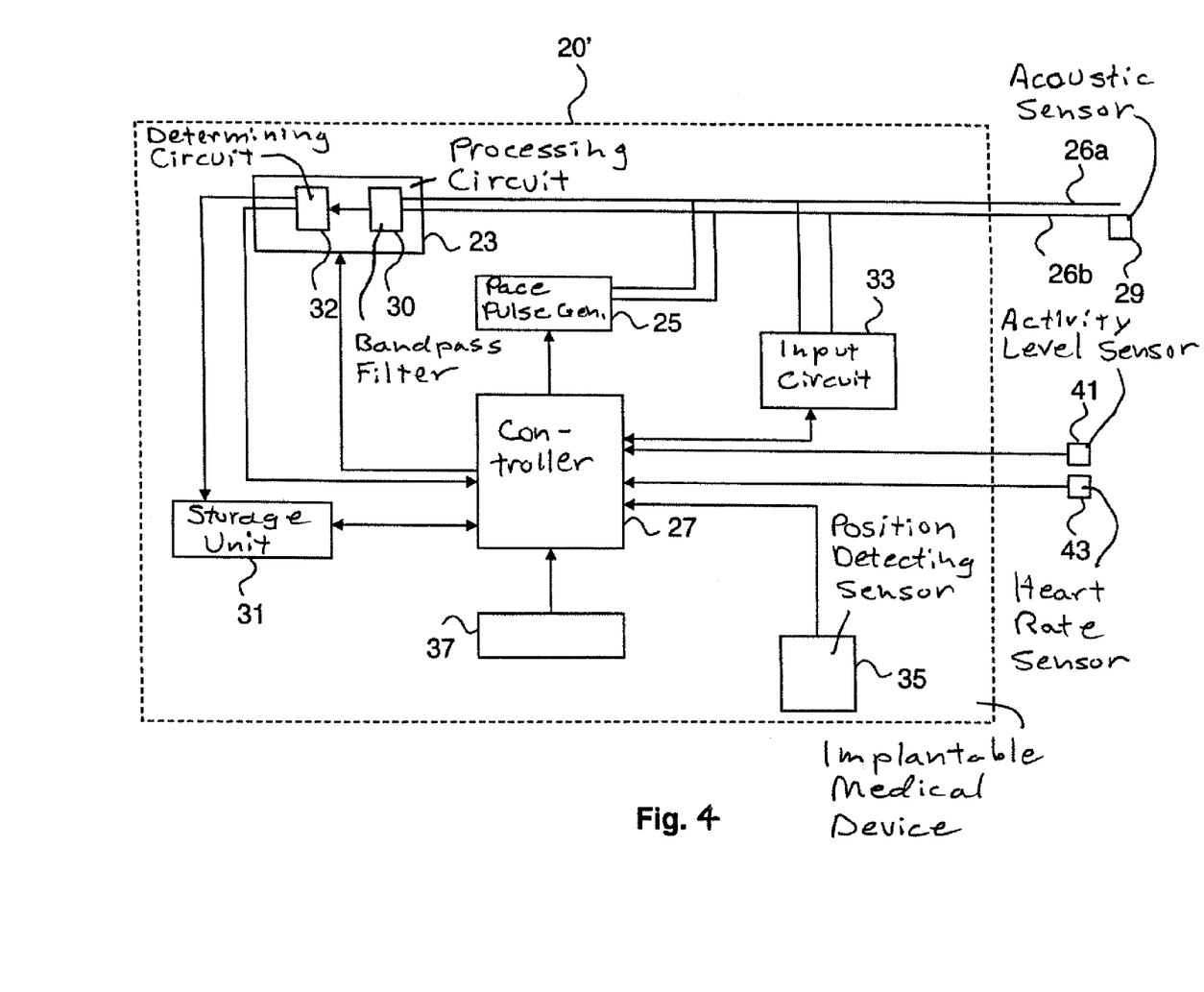
FIG. 4 is a block diagram of the primary functional components of another embodiment of the medical device according to the present invention.

With reference now to FIG. 4, another embodiment of the present invention will be described. Like parts in FIG. 2 and FIG. 3 are denoted with the same reference numeral and the description thereof will be omitted since they have been described with reference to FIG. 2. The implantable medical device 20' may include activity level sensing means 41 for sensing an activity level of the patient, which activity level sensing means is connected to the controller 27. The controller 27 may be adapted to determine whether a sensed activity level is below a predetermined activity level and to use also the activity level information in the detection of the condition or change of the condition. For example, if a high R value is detected, it may be an indication of either increased cardiac output at exercise or an increased stress level of the patient. In this case, a high activity level indicating that the patient is exercising can be used to distinguish between these two conditions. The controller 27 may be adapted to synchronize a sensing session of the acoustic sensor 29 with a determination that the sensed activity level is below a predetermined activity level or that the sensed activity level is within a activity level range between a second activity level and a third activity level. Thereby, it is possible to perform calculations of the relation R at stable conditions.

Furthermore, the implantable medical device 20' according to the present invention may comprise a position detecting sensor 35 arranged to detect a body position of the patient. For example, the position sensor 35 can adapted to detect a predetermined specific body position. In a one embodiment of the present invention, the position detecting means is a back-position sensor arranged to sense when the patient is lying on his/hers back (or on his or hers face). The position detecting sensor 35 is connected to the controller 27. The controller 27 may be adapted to determine whether the patient is in the at least one predetermined specific body position and to use the position information in the detection of the condition or change of the condition. In another embodiment, the controller 27 is adapted to synchronize a sensing session of the acoustic sensor 29 with a determination that the patient is in a predetermined position. Thereby, it is possible to perform calculations of the relation R at stable conditions.

Further, the implantable medical device 20' according to the present invention may include a heart rate sensor 43 for sensing a heart rate of the patient, which sensor 43 is connected to the controller 27. The controller 27 may be adapted to determine whether a sensed heart rate is within a predetermined heart rate interval. This heart rate information can be used in the detection of the condition or change of the condition. Moreover, the controller 27 may be adapted to synchronize a sensing session of the acoustic sensor 29 with a determination that the sensed heart rate level is within a predetermined heart rate level range, below a predetermined heart rate level or above a predetermined heart rate level. Thereby, it is possible to perform calculations of the relation R at stable conditions.

As will be apparent to those skilled in the art, only one, some of or all of the following features: the activity level sensing means 41, the heart rate sensor 43, or the position detector 35, may be included in the medical device according to the present invention. Thus, information from one, some of, or all of the above-mentioned sensors can be used in the detection.

Figure 5:
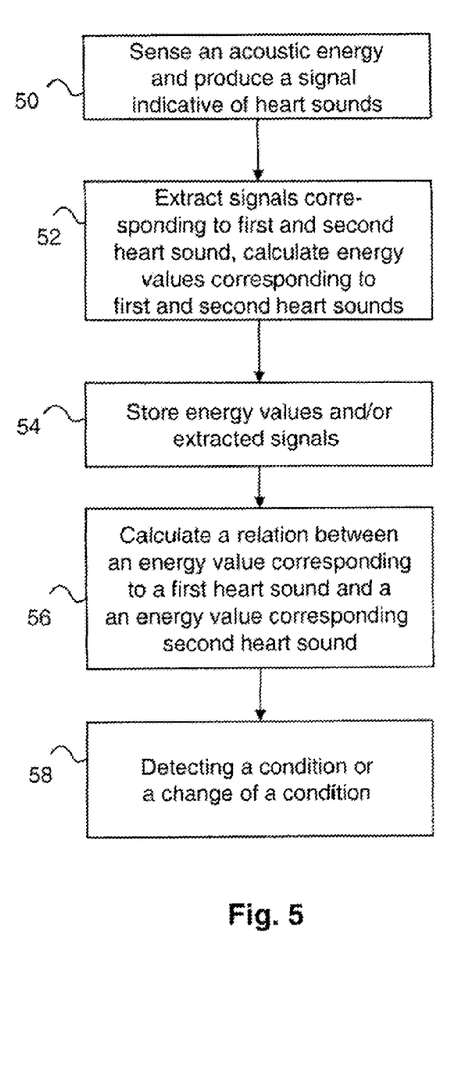
FIG. 5 is a flow chart of an embodiment of the method according to the present invention.
Figure 6A:
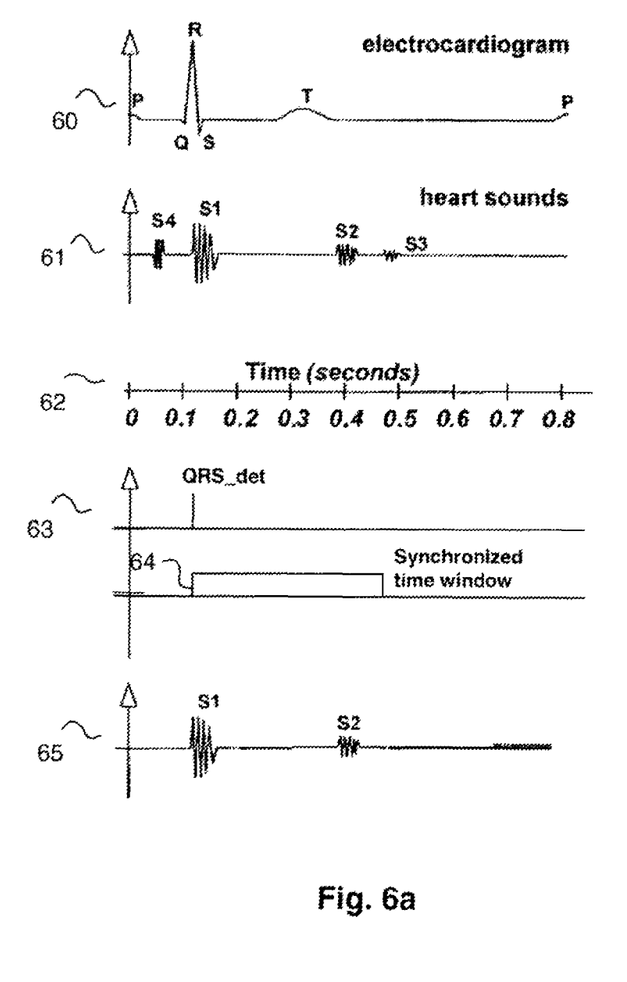
FIG. 6a shows a typical cardiac cycle at a heart rate of 75 BPM, related heart sounds, and the resulting signals in a one sensing procedure according to the present invention.
Figure 6B:
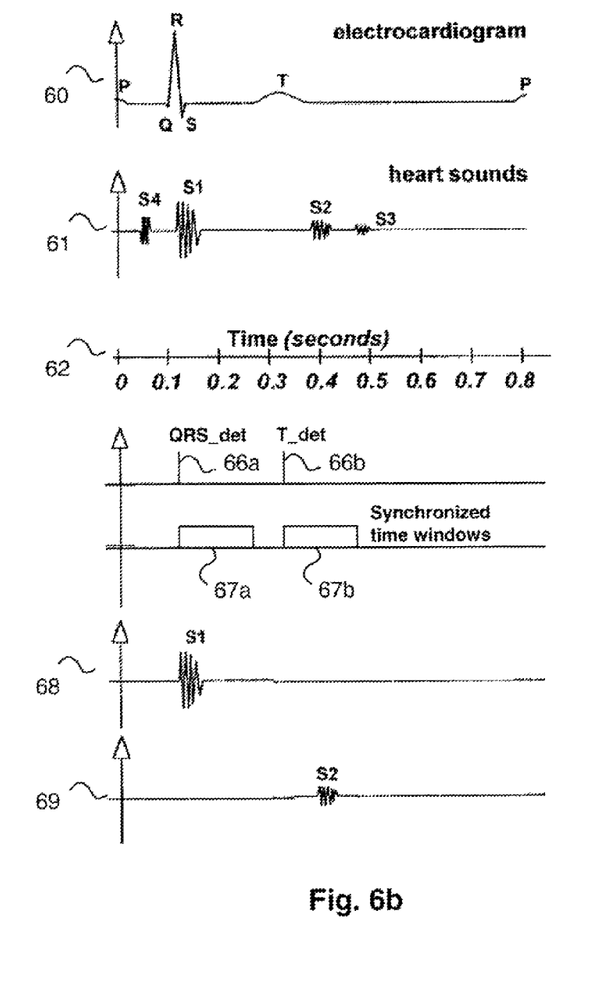
FIG. 6b shows a typical cardiac cycle at a heart rate of 75 BPM, related heart sounds, and the resulting signals in another sensing procedure according to the present invention.

Turning now to FIG. 5, a high-level description of the method according to the present invention will be given. First, at step 50, the acoustic sensor 29 senses an acoustic energy and produces signals indicative of heart sounds of the heart of the patient. This may be performed over predetermined periods of a cardiac cycle during successive cardiac cycles under control of the controller 27. The sensor 29 can be adapted to sense the acoustic energy during predefined time windows in the heart cycle. With reference now to FIGS. 6a and 6b, a typical cardiac cycle at a heart rate of 75 beats per minute (bpm), related heart sounds, and the resulting signals in two alternative sensing procedures according to the present invention are shown, respectively.

Referring first to FIG. 6a. A surface electrocardiogram and the related heart sounds S1, S2, S3, and S4 are indicated by 60 and 61, respectively, and a time axis is indicated by 62. In one embodiment, the acoustic sensor 29 is activated by a pacing pulse or the detection of a QRS-position, as indicated by 63 in FIG. 6a, an intrinsic detected event or a paced event indicated by 60. The acoustic sensor 29 senses the acoustic energy of the heart sound S1 and of the heart sound S2, indicated by 61, during a sensing session having a predetermined length, i.e. during predetermined time window, indicated by 64. In this embodiment, the initiation of the sensing session (i.e. the start of the time window) is synchronized with the detection of the QRS-position indicated by 63. The length of the time window is programmable and a typical length is about 400 ms. Hence, the acoustic sensor 29 receives a triggering signal from the controller 27 upon detection of the QRS-position by the input circuit 33. The produced signal corresponding to the first heart sound S1 and the second heart sound S2 is indicated by 65. This may be performed during successive cardiac cycles under control of the controller 27, which thus produces a time series of successive heart sound signals. The produced signal or signals indicative of the first heart sound and the second heart sound are then supplied to the signal processing circuit 23 where, as will be described below in further detail, a signal or signals corresponding to a first heart sound (S1) and a second heart sound (S2) are extracted from the sensed signal by the pre-processing circuits 30, 32.

Turning now to FIG. 6b, the same surface electrocardiogram and the related heart sounds S1, S2, S3, and S4 as in FIG. 6a are shown but the sensing procedure is performed in a alternative way. The surface electrocardiogram and the related heart sounds S1, S2, S3, and S4 are hence indicated by 60 and 61, respectively, and the time axis is indicated by 62. In this embodiment, the acoustic sensor 29 is activated by the detection of a QRS-position and by the detection of a T-position, as indicated by 66a and 66b, respectively, in FIG. 6b, which may be intrinsic detected events or paced events. The acoustic sensor 29 senses the acoustic energy in the heart sound S1, indicated by 61, during a first sensing session or predetermined time window 67a. In this embodiment, the initiation of the first sensing session is synchronized with the detection of the QRS-position. The length of the time window is programmable and a typical length is about 200 ms. Moreover, the acoustic sensor 29 senses the acoustic energy in the heart sound S2, indicated by 61, during a second sensing session or predetermined time window 67b. In this embodiment, the initiation of the second sensing session is synchronized with the detection of the T-position. The length of the time window is programmable and a typical length is about 200 ms. Hence, the acoustic sensor 29 receives a first triggering signal from the controller 27 upon detection of the QRS-position by the input circuit 33 and a second triggering signal from the controller 27 upon the detection of the T-position. The produced signals corresponding to the first heart sound S1 and the second heart sound S2 are indicated by 68 and 69, respectively. This may be performed during successive cardiac cycles under control of the controller 27, which thus produces a time series of successive heart sound signals. The produced signals indicative of the first heart sounds and second heart sounds are then supplied to the signal processing circuit 23 where, as will be described below in further detail, a signal corresponding to a first heart sound (S1) and a signal corresponding to the second heart sound (S2) are extracted from a sensed signal by the pre-processing circuits 30, 32. The signal or signals indicative of heart sounds are supplied to the signal processing circuit 23 where, at step 52, signals corresponding to a first heart sound (S1) and a second heart sound (S2) are extracted from a sensed signal of a cardiac cycle and an energy value (E1) corresponding to a first heart sound (S1) and an energy value (E2) corresponding to a second heart sound (S2) are calculated using the extracted signals.

Optionally, this step may include performing a filtering procedure in order to filter the sensed signal. In one embodiment, a first heart sound signal is determined to be a part of the sensed signal having an amplitude above a predetermined amplitude level and a second heart sound signal is determined to be a part of the sensed signal above a second predetermined amplitude level. Then, in order to calculate the energy values E1 and E2, the first and second heart sound signals, respectively, are integrated, for example, over predetermined time windows. Alternatively, the sensed signal can be integrated over a first time window to calculate an energy value (E1) corresponding to the first heart sound and over a second time window to calculate an energy value (E2) corresponding to the second heart sound and in this case the filtering procedure is thus not necessary.

Figure 7:
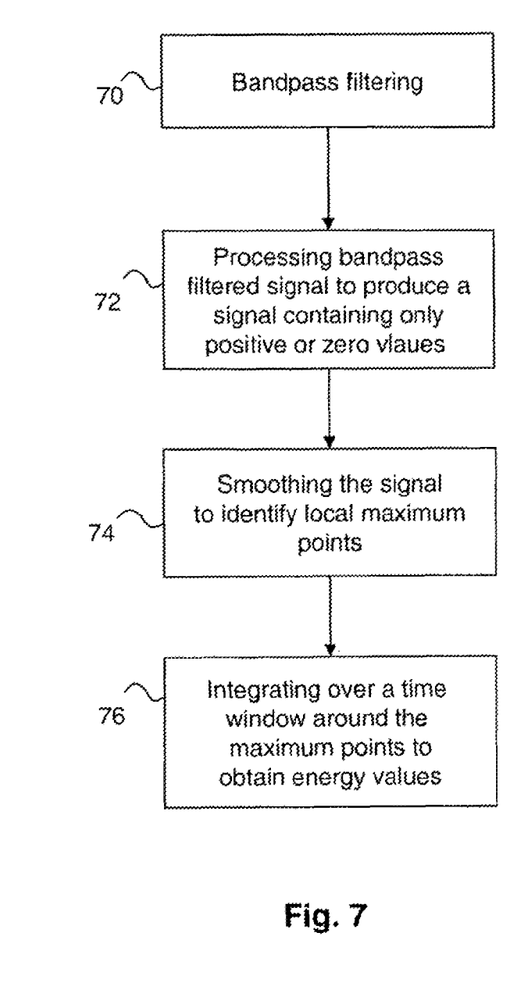
FIG. 7 shows signal processing steps performed in accordance with an embodiment of the method according to the present invention.

Another embodiment of the filtering procedure will now be discussed with reference to FIGS. 3b, 3c and 7. First, at step 70, the sensed signal is bandpass filtered. In one embodiment, two bandpass filters 34a and 34b are used, see FIG. 3c. A first filter 34a adapted to receive a first heart sound signal waveform, see 68 in FIG. 6b, and to cut out a frequency range of 20-40 Hz to form a signal corresponding to the first heart sound (S1) and a second filter 34b adapted to receive a second heart sound signal waveform, see 69 in FIG. 6b, and to cut out a frequency range of 10-300 Hz to form a signal corresponding to the second heart sound (S2). Alternatively, one bandpass filter 42 is used, see FIG. 3c. The filter 42 is adapted to receive a heart sound signal waveform comprising both the first and the second heart sound signal, see 65 in FIG. 6a, and to cut out a frequency range of 10-300 Hz to form a signal containing the first heart sound (S1) and the second heart sound (S2), see signal waveform 65 in FIG. 6a. The bandpass filtering process is performed as a zero-phase procedure to cancel out time delays introduced by the filters. The sensed signal is in fact filtered twice, first in the forward direction and second in the backward direction. Then, at step 72, the bandpass filtered signals are processed to obtain a signal containing only positive or zero values, for example, in the absolute value determining means 36 or a rectifier. Alternatively, the signals can be squared in a squaring means resulting in signal corresponding to the instantaneous power of the bandpass filtered signals. Thereafter, at step 74, a smoothing procedure of the signals is performed in the identifying means 38 to identify at least one local maximum point being coincident with a first heart sound signal and at least one local maximum point being coincident with a second heart sound signal. The smoothed signals are then fed to the integrator 40 where, at step 76, the first heart sound signal is integrated over a predetermined time window comprising the at least one local maximum point to form an energy value (E1) corresponding to the first heart sound and the second heart sound signal is integrated over a predetermined time window encompassing the at least one local maximum point to form an energy value (E2) corresponding to the second heart sound.

Returning now to FIG. 5, at step 54, the energy values E1 and E2 corresponding to the first heart sound signal and the second heart sound signal, respectively, and/or the extracted signals are stored in the memory means 31. If energy values corresponding to the first heart sound signal and the second heart sound signal are obtained for successive cardiac cycles, the values can be stored in the memory means 31 in consecutive time order. These values can be buffered to be used only in the calculation of the energy values or can be stored for use in the detection of a condition or a change of condition.

Subsequently, at step 56, a relation, R=E1/E2, between the energy value (E1) corresponding to the first heart sound and the energy value (E2) corresponding to the second heart value is calculated. This can be performed within a single heart beat or on a continuous basis for successive cardiac cycles and thereby it is possible to obtain a trend of the relation R over time. The calculated relations R=E1/E2 can be stored in the memory means 31 and/or transferred to a programmer (not shown) via a programmer interface (not shown).

At step 58 the calculated relation R=E1/E2 is used to detect or derive a certain condition or a change of the condition including heart insufficiency, systemic hypertension, pulmonary hypertension, myocardial ischemia, increased cardiac output and/or increased stress level. The calculated relations R=E1/E2 reflect, as discussed above, the mitral valve energy compared to the aortic valve energy. If R becomes small it may thus be caused by a low E1 and/or a high E2. A low E1 may under this condition (i.e. a small R) be an indication of, for example, mitral regurgitation, a long PV interval (AV block III) or heart insufficiency and a high E2 may under this condition (i.e. a small R) be an indication of, for example, systemic pulmonary hypertension. The R-value will also decrease at myocardial ischemia, which may be used to detect silent ischemia. If R becomes high it may thus be caused by a high E1 and/or a low E2. A high E1 may under this condition (i.e. a high R) indicate, for example, increased cardiac output (CO), tachycardia, left ventricle hypertrophy, mitral stenosis, or a short PR interval. On the other hand, a small E2 (at a high R) may be an indication of aortic pulmonary stenosis.

In one embodiment, a present relation R=E1/E2 is compared with preceding relations R, i.e. relations R corresponding to heart sounds of preceding cardiac cycles, to detect a certain condition or a change of the condition including heart insufficiency, systemic hypertension, pulmonary hypertension, myocardial ischemia, increased cardiac output and/or increased stress level. Thus, the relation R=E1/E2 is a relative value that is compared with values in the pre-history. It is also possible to monitor the variability of the relation and the individual energy values. A high variability may indicate that filling is altering due to e.g. arrhythmia or conduction disorder. In another embodiment, a present relation R=E1/E2 is compared with a predetermined reference value to detect a certain condition or a change of the condition. Furthermore, it is also possible to compare calculated R values with predetermined reference values stored in the memory means 31, which may be programmable.

In order to increase the accuracy, a condition check may be performed, for example, at step 56 or at step 58. In one embodiment, a present condition is checked, for example, the present activity level of the patient, which is used in the detection of the condition. It is, for example, possible to monitor the variability of the relation and the individual energy values. A high variability during otherwise stable conditions (e.g. at rest) may indicate that filling is altering due to e.g. arrhythmia or conduction disorder. Moreover, if it is found that the activity level of the patient is increased and R is high (E1 is high), it may be an indication of increased cardiac output at exercise instead of an indication of stress since the increased activity level indicates exercise. In another embodiment, it is checked whether predetermined conditions, such as activity level of the patient or position of the patient, are fulfilled. If the predetermined conditions are not fulfilled, the calculated relation R=E1/E2 may be rejected. This check may include, in case the medical device comprises a position sensor, to determine whether the patient is in a predetermined specific body position. In further embodiments, a certain sensed condition may be synchronized with a sensing session of the acoustic sensor, as discussed above.

As will be apparent to those skilled in the art, certain steps discussed above need not be performed in the order described above. For example, the step of storing calculated energy values and/or extracted signals can be performed partly before step 54, i.e. the extracted signals can be stored before step 56 is executed and the energy values can be stored after step 56 is executed.

Although modifications and changes may be suggested by those skilled in the art, it is the intention of the inventors to embody within the patent warranted heron all changes and modifications as reasonably and properly come within the scope of their contribution to the art.

We claim as our invention:

1. An implantable medical device for detecting a condition of a heart of a patient, said device comprising:

a pulse generator that emits cardiac stimulating pacing pulses;

a lead comprising at least one electrode, said lead being connected to said pulse generator and being configured for implantation in the patient to deliver said cardiac stimulating pacing pulses to cardiac tissue in the patient;

an acoustic sensor configured to sense acoustic energy in the patient, said acoustic sensor emitting an acoustic sensor signal indicative of heart sounds produced by the heart of the patient;

a signal processor connected to said acoustic sensor configured to extract signal components from said acoustic sensor signal respectively corresponding to a first heart sound, known as the first heart sound S1, and a second heart sound, known as the second heart sound S2, over predetermined periods of a cardiac cycle during successive cardiac cycles, and to calculate a first energy value E1 corresponding to said first heart sound S1 and a second energy value E2 corresponding to said second heart sound S2;

a storage unit in communication with said signal processor that stores said first and second energy values E1 and E2 corresponding to said first and second heart sounds S1 and S2; and a controller connected to said pulse generator, and configured to calculate a quotient E1/E2 for successive cardiac cycles, and to use said quotient E1/E2 to identify a condition of the heart of the patient or a change of said condition of the heart of the patient, and to control emission of said cardiac stimulating pacing pulses from said pulse generator dependent on said condition or said change of said condition.

2. An implantable medical device as claimed in claim 1 wherein said controller is configured to compare said quotient E1/E2 with at least one preceding quotient E1/E2 to identify said condition or said change of said condition.

3. An implantable medical device as claimed in claim 1 wherein said signal processor is configured to calculate said first energy E1 value as a mean value over a predetermined number of successive first energy values E1 corresponding to successive first heart sounds S1 and to calculate said second energy value E2 as a mean value over a predetermined number of successive second energy values E2 corresponding to successive second heart sounds S2, and wherein said controller is configured to calculate a relation between a maximum amplitude of said first heart sound S1 and a maximum amplitude of said second heart sound S2 of a cardiac cycle for successive cardiac cycles, and to compare a present relation with at least one preceding relation, to obtain a comparison result, and to use said comparison result in addition to said quotient E1/E2 to detect said condition or said change of said condition.

4. An implantable medical device as claimed in claim 1 wherein said controller calculates said first energy value E1 as a mean value over a predetermined number of successive first energy values E1 corresponding to successive first heart sounds S1 and to calculate said second energy value E2 as a mean value over a predetermined number of successive second energy values E2 corresponding to successive second heart sounds S2, and to calculate said relation as a mean value of relations over a predetermined number of successive relations corresponding to said successive first and second heart sounds S1 and S2.

5. An implantable medical device as claimed in claim 4 wherein said controller is configured to detect said condition or said change of said condition as a condition selected from the group consisting of heart insufficiency, systemic hypertension, pulmonary hypertension, myocardial ischemia, increased cardiac output, and increased stress level.

6. An implantable medical device as claimed in claim 1 wherein said controller is configured to compare a present first energy value E1 with a preceding first energy value E1, and to compare a present second energy value E2 with a preceding second energy value E2 to calculate said relation.

7. An implantable medical device as claimed in claim 1 wherein said signal processor comprises a component that extracts said signal components respectively corresponding to said first heart sound S1 and said second heart sound S2, said component being selected from the group consisting of:
  a determining unit that determines said component corresponding to said first heart sound S1 as being above a first amplitude level of said acoustic sensor signal, and that determines said component corresponding to said second heart sound S2 as being above a second amplitude level of said acoustic sensor signal; and
  an integrator that integrates said acoustic sensor signal during a first predetermined time window to obtain said first energy value E1 as an integration result, and that integrates said acoustic sensor signal during a second predetermined time window to obtain said second energy value E2 as an integral result.

8. An implantable medical device as claimed in claim 1 wherein said signal processor comprises:
  a bandpass filter that filters out frequency components of said acoustic sensor signal outside of a predetermined frequency range, to obtain a filtered signal;
  a positive/zero value generator selected from the group consisting of a rectifier that rectifies said filter signal to produce signals containing only positive values or zero values, and a squaring circuit that performs a squaring of said filtered signal to produce a signal containing only positive values or zero values;
  an identifying circuit configured to identify at least one first local maximum point coincident with said first heart sound signal S1 and at least one second local maximum point coincident with said second heart sound signal S2; and
  an integrator that integrates said signal containing only positive values or zero values from said positive/zero value generator in a predetermined time window comprising said at least one first local maximum point to obtain said first energy value E1 as an integration result, and that integrates said signal containing only positive values or zero values from said positive/zero value generator in a predetermined time window comprising said at least one second local maximum point to obtain said second energy value E2 as an integration result.

9. An implantable medical device as claimed in claim 1 comprising:
  a position detector configured to detect a body position of the patient, represented in a position detector output signal; and
  said controller being supplied with said position detector output signal and being configured to determine, from said position detector output signal, patient information indicating whether said patient is in at least one predetermined body position, and to use said position information, in addition to said quotient E1/E2, to determine said condition or said change of said condition, and to synchronize sensing by said acoustic sensor with said patient being in said predetermined body position.

10. An implantable medical device as claimed in claim 1 comprising:
  an activity level sensor that senses an activity level of the patient, and that emits an activity level signal corresponding to said activity level; and
  said controller being supplied with said activity level signal and being configured to determine whether said activity level is below a predetermined activity level or to determine whether said activity level is below a predetermined first activity level or within an activity level range between a second activity level and a third activity level, and to synchronize sensing by said acoustic sensor dependent on whether the sensed activity level is below said predetermined activity level, or within said activity level range.

11. An implantable medical device as claimed in claim 1 comprising;
  a heart rate sensor that senses a heart rate of the patient, and that emits a heart rate signal representing said heart rate; and
  said controller being supplied with said heart rate signal and being configured to determine whether said heart rate is within a predetermined heart rate range, as heart rate information, and to use said heart rate information, in addition to said quotient E1/E2, to detect said condition or said change of said condition.

12. An implantable medical device as claimed in claim 1 wherein said acoustic sensor is located at a location selected from the group consisting of at a housing of said device, at a lead of said device configured for placement in a ventricle of the heart, at a lead of said device configured for placement in a coronary vein of the heart, and wherein said acoustic sensor is a sensor selected from the group consisting of accelerometers, pressure sensors and microphones.

13. A method for detecting a condition of a heart of a patient using an implantable medical device, comprising the steps of:
sensing an acoustic energy in the patient to obtain a sensed signal indicative of heart sounds of the patient over predetermined periods of a cardiac cycle during successive cardiac cycles;
in said implantable medical device, extracting signal components from said sensed signal respectively corresponding to a first heart sound, known as the first heart sound S1, and a second heart sound, known as the second heart sound S2, of a cardiac cycle;
in said implantable medical device, calculating a first energy value E1 corresponding to said first heart sound S1 and a second energy value E2 corresponding to said second heart sound S2;
in said implantable medical device, storing said first and second energy values E1 and E2; and
in said implantable medical device, calculating a quotient E1/E2 and, dependent on said quotient E1/E2, detecting said condition or a change of said condition.

14. A method as claimed in claim 13 comprising comparing a present quotient E1/E2 with at least one preceding quotient E1/E2 to detect said condition or said change of said condition.

15. A method as claimed in claim 13 comprising calculating, as said quotient E1/E2, a quotient between a maximum amplitude of said first energy value E1 and a maximum amplitude of said second energy value E2.

16. A method as claimed in claim 13 comprising calculating said first energy value E1 as a mean value over a predetermined number of successive first energy values E1 corresponding to successive first heart sounds S1 and calculating said second energy value E2 as a mean value over a predetermined number of successive second energy values E2 corresponding to successive second heart sounds S2, and comprising calculating said quotient as a mean value over said predetermined number of successive first and second energy values E1 and E2.

17. A method as claimed in claim 13 comprising from said quotient E1/E2, detecting said condition or said change of said condition as a condition selected from the group consisting of heart insufficiency, systemic hypertension, pulmonary hypertension, myocardial ischemia, increased cardiac output, and increased stress level.

18. A method as claimed in claim 13 comprising extracting said component corresponding to said first heart sound S1 from said sensed signal as having an amplitude above a predetermined first amplitude level, and extracting said component corresponding to said second heart sound S2 from said sensed signal as being above a predetermined second amplitude level, and calculating said first energy value E1 by integrating said component corresponding to said first heart sound S1 during a predetermined first time window, and calculating said energy value E2 by integrating said component corresponding to said second heart sound S2 over a predetermined second time window.

19. A method as claimed in claim 13 comprising calculating said relation by:
filtering out frequency components of said sense signal outside of a predetermined frequency range, to obtain a filtered signal;
producing signals containing only positive or zero values by rectifying said filtered signal or by squaring said filtered signal;
identifying at least one first local maximum point coincident with said first heart sound S1 and identifying at least one second local maximum point coincident with said second heart sound S2; and
integrating said component corresponding to said first heart sound S1 in a predetermined time window comprising said at least one first local maximum point to obtain said first energy value as an integration result, and integrating said component corresponding to said second heart sound S2 in a predetermined time window comprising said at least one second local maximum point to obtain said second energy value as an integration result.

20. A method as claimed in claim 13 comprising:
detecting at least one body position of the patient;
determining when said patient is in said at least one predetermined body position; and
synchronizing sensing by said acoustic sensor to obtain said sensed signal when said patient in said predetermined body position.

21. A method as claimed in claim 13 comprising:
sensing an activity level of the patient;
determining whether the activity level is below predetermined activity level or whether said activity level is below a predetermined first activity level or within an activity level range between a second activity level and third activity level; and
synchronizing sensing of said acoustic signal dependent on whether said activity level is below said predetermined activity level or said sensed activity level is within said activity level range.

22. A method as claimed in claim 13 comprising:
sensing a heart rate of the patient;
determining whether said heart rate is within a predetermined heart rate range; and
if said heart rate is within said predetermined heart rate range, calculating said relation.

23. A method as claimed in claim 13 comprising detecting said acoustic signal from a location selected from the group consisting of at a housing said implantable medical device, in a right ventricle of the heart, and in a coronary vein of the heart and sensing said acoustic signal with an acoustic sensor selected from the group consisting of accelerometers, pressure sensors, and microphones.

* * * * *